US009200137B2

(12) United States Patent
Arendt et al.

(10) Patent No.: US 9,200,137 B2
(45) Date of Patent: Dec. 1, 2015

(54) COMPOSITIONS COMPRISING STRUCTURAL ISOMERS OF 1,4-CYCLOHEXANEDIMETHANOL DIBENZOATE AND POLYMER COMPOSITIONS CONTAINING SAME

(71) Applicant: Eastman Specialties Holdings Corporation, Kingsport, TN (US)

(72) Inventors: William D Arendt, Libertyville, IL (US); Makarand V Joshi, Grayslake, IL (US); Yvonne Aileen Berry-Walker, Elkhorn, WI (US); Paul Steven Lakomiak, DeKalb, IL (US); Mirnahini Jeganathan, Lake Villa, IL (US)

(73) Assignee: Eastman Specialties Holdings Corporation, Kingsport, TN (US)

( * ) Notice: Subject to any disclaimer, the term of this patent is extended or adjusted under 35 U.S.C. 154(b) by 0 days.

(21) Appl. No.: 13/870,176

(22) Filed: Apr. 25, 2013

(65) Prior Publication Data

US 2013/0237939 A1 Sep. 12, 2013

Related U.S. Application Data

(62) Division of application No. 11/949,378, filed on Dec. 3, 2007, now abandoned.

(51) Int. Cl.
| | |
|---|---|
| *C08K 5/10* | (2006.01) |
| *C08K 5/12* | (2006.01) |
| *A61F 13/15* | (2006.01) |
| *C08L 23/02* | (2006.01) |
| *C08L 23/08* | (2006.01) |
| *C09J 123/02* | (2006.01) |
| *C07C 69/78* | (2006.01) |
| *C07C 67/293* | (2006.01) |
| *C07C 37/52* | (2006.01) |
| *B32B 7/04* | (2006.01) |
| *C08K 5/103* | (2006.01) |
| *C08L 91/00* | (2006.01) |

(52) U.S. Cl.
CPC .............. *C08K 5/12* (2013.01); *A61F 13/15203* (2013.01); *B32B 7/04* (2013.01); *C07C 37/52* (2013.01); *C07C 67/293* (2013.01); *C07C 69/78* (2013.01); *C08L 23/02* (2013.01); *C08L 23/0853* (2013.01); *C09J 123/02* (2013.01); *C07B 2200/09* (2013.01); *C07C 2101/14* (2013.01); *C08K 5/10* (2013.01); *C08K 5/103* (2013.01); *C08L 91/00* (2013.01); *C08L 2314/06* (2013.01); *Y10T 442/3667* (2015.04); *Y10T 442/3854* (2015.04); *Y10T 442/673* (2015.04); *Y10T 442/674* (2015.04)

(58) Field of Classification Search
CPC ............ C08K 5/10; C08K 5/12; C08L 23/02; C08L 23/0853; C08L 25/08; C08L 65/02; C07C 67/52; C07C 67/293; C07C 69/78
USPC .......... 524/270, 272, 274, 285, 287, 292, 293, 524/299, 396
See application file for complete search history.

(56) References Cited

U.S. PATENT DOCUMENTS

| | | | |
|---|---|---|---|
| 4,349,469 | A | 9/1982 | David et al. |
| 4,999,090 | A | 3/1991 | Tateno et al. |
| 5,534,575 | A | 7/1996 | Foster et al. |
| 5,624,986 | A | 4/1997 | Bunnelle et al. |
| 5,747,573 | A | 5/1998 | Ryan |
| 6,682,587 | B2 | 1/2004 | Hendricks et al. |
| 2002/0086154 | A1 | 7/2002 | Miller et al. |
| 2002/0124771 | A1 | 9/2002 | Hendricks et al. |
| 2002/0193474 | A1 | 12/2002 | Daily et al. |
| 2004/0127609 | A1 | 7/2004 | Strand et al. |
| 2005/0064180 | A1 | 3/2005 | Daily et al. |
| 2009/0142981 | A1 | 6/2009 | Arendt et al. |

FOREIGN PATENT DOCUMENTS

| | | |
|---|---|---|
| JP | 03-059086 | 3/1991 |
| JP | 05-186378 | 7/1993 |

OTHER PUBLICATIONS

Clark, Stereoisomerism—Geometric Isomerism. [Online] Jul. 2007, Retrieved from the internet <http://web.archive.org/web/20071024134305/http://www.chemguide.co.uk/basicorg/isomerism/geometric.html>; 9 pgs.
International Search Report dated Jan. 27, 2009 received for international application No. PCT/US08/84279.

*Primary Examiner* — David W Wu
*Assistant Examiner* — Marie Reddick
(74) *Attorney, Agent, or Firm* — Jennifer R. Knight

(57) ABSTRACT

Novel solid benzoate ester compositions are mixtures comprising the trans- and cis-structural isomers of 1,4-cyclohexanedimethanol dibenzoate wherein the trans isomer constitutes from 1 to 66 or from 72 to 99 weight percent of the mixture. The properties imparted to a variety of polymer compositions, including hot melt adhesives, cannot be achieved using the commercially available mixture of these isomers.

4 Claims, 2 Drawing Sheets

COMPOSITIONS COMPRISING STRUCTURAL ISOMERS OF 1,4-CYCLOHEXANEDIMETHANOL DIBENZOATE AND POLYMER COMPOSITIONS CONTAINING SAME

CROSS-REFERENCE TO RELATED APPLICATIONS

This application is a divisional application of U.S. Non Provisional Application Ser. No. 11/949378 filed on Dec. 3, 2007, now abandoned, and which is hereby incorporated by this reference in its entireties.

FIELD OF THE INVENTION

This invention relates to novel mixtures containing two structural isomers of 1,4-cyclohexanedimethanol dibenzoate in controlled portions. More particularly this invention relates to a method for preparing these isomeric mixtures and the use of these mixtures to impart desirable properties to a variety of polymer compositions including but not limited to hot melt adhesives.

DESCRIPTION OF THE PRIOR ART

The dibenzoate of 1,4-cyclohexanedimethanol, hereinafter referred to as CHDM, exists in two isomeric forms. One of these is a trans form that can be represented by the formula

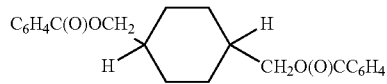

The second is a cis form that can be represented by the formula

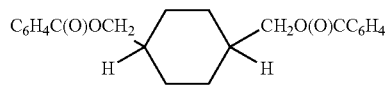

It has been found that the cyclohexane ring in both of these isomers is in the "chair" form to avoid steric interactions between the bulky methylbenzoate groups.

One commercial process for preparing 1,4-cyclohexanedimethanol, the starting material for preparing the dibenzoate, involves hydrogenation of 1,4-cyclohexanedicarboxylic acid or an ester of this acid to the corresponding dialcohol. The isomeric distribution in the resultant mixture of cis and trans isomers is determined by the starting materials and hydrogenation catalyst. U.S. Pat. No. 6,919,489, which issued to Orth et al. uses a Raney nickel catalyst doped with rhenium to obtain CHDM with a cis to trans ratio of 0.7 or less from the dimethyl ester of the corresponding dicarboxylic acid having a cis to trans ratio of 1.2 to 2.1.

Other patents disclosing the ability to control the cis to trans ratio of CHDM by adjusting the conditions or molar ratio of hydrogen to a dialkyl ester of 1,4-cyclohexanedicarboxylic acid include U.S. Pat. Nos. 5,395,986 and 5,395,987.

Methods for separating the cis- and trans-stereoisomers of CHDM are reported in the literature. Malachowski et al (Ber. 1938, 71, 159 accomplish this by reducing diethyl hexahydroterephthalate with sodium and alcohol. From either the cis- or trans-hexahydro ester a stereoisomeric mixture of the corresponding alcohol was obtained. The cis- and trans esters in the mixture were separated by conversion to the corresponding benzoates followed by fractional crystallization and hydrolysis.

The present invention is based on the discovery of a method for separating a commercially available version of CHDM dibenzoate containing about 70 weight percent of the trans isomer and about 30 weight percent of the cis isomer into fractions containing up to 100 percent by weight of either isomer. Mixtures containing from 1 to 66 weight percent or from 72 to 99 weight percent of the trans isomer have not been reported in the literature and are therefore considered novel compositions.

The present inventors have discovered that the properties imparted to polymer compositions, particularly hot melt adhesives, by the present benzoate ester mixtures will vary considerably depending upon the relative concentrations of trans and cis isomers in the mixture.

U.S. Pat. No. 5,026,756 to William D. Arendt discloses that the distinguishing feature of the compound referred to in the patent as the dibenzoate of 1,4-cyclohexanedimethanol (hereinafter CHDMDB) relative to other esters of benzoic acid is the existence of a well-defined freezing point. When heated above their melting points and then allowed to cool to below this temperature most other dibenzoates will typically remain liquid at temperatures substantially below their melting points, a phenomenon referred to as "supercooling".

The ability to reproducibly solidify makes the isomers of CHDMDB uniquely suitable for use in hot melt adhesives. The aforementioned Arendt patent contains the curve produced when a sample of CHDMDB is heated in a differential scanning calorimeter. The curve is described as bimodal, with melting points at "about 80 and 123° C." The higher melting point is more sharply defined.

The CHDMDB described in the aforementioned Arendt patent is prepared from a commercially available product containing about 68 weight percent of the trans isomer and about 32 weight percent of the cis-isomer of CHDM.

The present invention is based on the discovery that when a mixture of CHDMDB isomers referred to in the aforementioned Arendt patent is heated above its melting point and then gradually cooled, a partial solidification in the form of a crystalline material occurs at a temperature of about 100° C. Analysis of this crystalline material by gas chromatography reveals that it is a mixture typically containing more than 90 weight percent of the trans isomer. The remainder of the molten material solidifies below about 70° C. to a non-crystalline material containing approximately equal weights of the trans and cis isomers.

It has also now been found that the present trans- and cis-rich mixtures impart different properties to polymer compositions in general and to hot melt adhesives in particular. By using one of the present CHDMDB mixtures containing more than about 72 percent by weight of the trans isomer as a modifier both the open time and the time required for the adhesive to achieve its ultimate properties are substantially reduced relative to the values obtained using the isomer distribution of the product described in the Arendt patent. The second of these advantages allows for a substantial increase in the maximum speed of a production line on which hot melt adhesives are used to bond two layers of paper, cardboard, fabric or other material. It was also found that adhesives containing a mixture with more than about 72 weight percent of the trans isomer can be designed to be significantly stronger than adhesives based on prior art modifiers.

Open time is the time interval during which the adhesive applied to the first substrate remains sufficiently adhesive to effect a bond between this substrate and a second one applied to it. Set time is defined as the time required for bonding once the two substrates to be joined are pressed together.

SUMMARY OF THE INVENTION

This invention provides novel solid benzoate ester compositions containing both the cis and trans isomers of 1,4-cyclohexane dimethanol dibenzoate wherein the trans isomer constitutes from 1 to 66 or from 72 to 99 weight percent of the compositions. A preferred composition contains 90 to 94 weight percent of the trans isomer, and most preferably more than 95 weight percent of the trans isomer. In another aspect the composition includes 48 to 52 weight percent of the trans isomer.

This invention also provides a method for separating a commercially available form of 1,4-cyclohexane dimethanol dibenzoate (CHDMDB) using melt refining into a crystalline solid composition containing from 72 to about 99 weight percent of the trans isomer of 1,4-cyclohexanedimethanol dibenzoate and a partially crystalline solid containing from 1 up to about 66 weight percent of this trans isomer.

A third aspect of the present invention provides a wide variety of polymer compositions containing any of the isomer mixtures of this invention as a plasticizer or other type of modifier. Depending upon the type(s) of polymer(s) and other ingredients present, the ester compositions of this invention impart a variety of desirable properties to polymer compositions.

Hot melt adhesives constitute a preferred class of polymer compositions of this invention. These compositions typically comprise 1) a polymer typically selected from the group consisting of olefinic polymers, including but not limited to ethylene/vinyl acetate copolymers and styrene/olefin copolymers, 2) at least one hydrocarbon resin and 3) one of the present CHDMDB isomer mixtures as a modifier.

Benzoate ester compositions of this invention containing more than about 72 weight percent of the trans isomer of 1,4-cyclohexanedimethanol dibenzoate typically decrease set times and can increase bond strength of hot melt adhesives, among other advantages. Ester compositions of this invention containing less than about 66 weight percent of this trans isomer can increase open time of these adhesives in addition to providing other advantages.

DETAILED DESCRIPTION OF THE INVENTION

Figure 1:
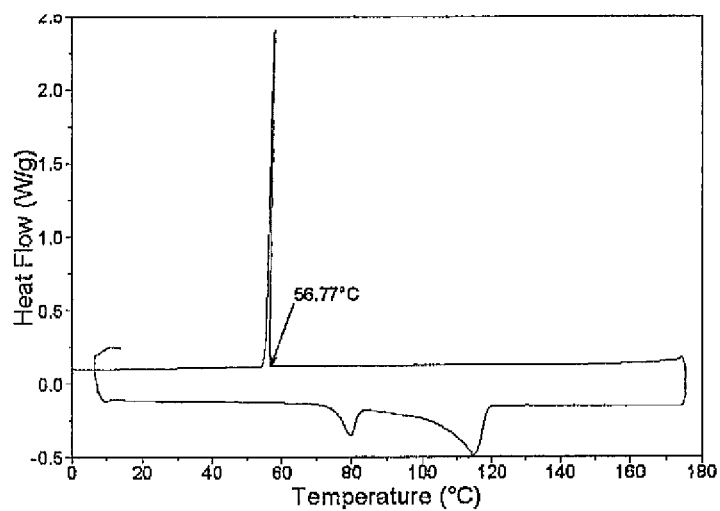
FIG. 1 is a DSC trace of commercially available CHDMDB, Benzoflex 352.

The novel benzoate ester mixtures of this invention are prepared by melt refining using the following series of process steps:
1. A commercially available mixture containing about 68 to about 70 weight percent of the trans and about 30 to about 32 weight percent of the cis isomers of CHDMDB is heated to a temperature above the melting point of the mixture to form a molten material which is then allowed to gradually cool to about 100° C., at which point crystallization of a portion of the material occurs. The melting point will be in the range of about 120 to about 128. The relative concentrations of trans and cis isomers in the crystallized material will be determined by the rate of cooling to the crystallization temperature and the time interval during which the mixture of molten and crystalline materials is maintained at this temperature. For example, cooling for 1 hour resulted in formation of 84-86% trans isomer and cooling for 16 hours resulted in formation of 94-96% trans isomer.
2. The crystalline material containing up to 97 weight percent of the trans isomer of CHDM dibenzoate is isolated from the mixture.
3. The remaining liquid material is allowed to cool to ambient temperature to obtain a solid containing substantially equal weights of the trans and cis isomers.

The CHDMDB used as a starting material to obtain the isomeric mixtures of this invention can be prepared by reacting benzoic acid or a suitable derivative thereof with one of the commercially available forms of 1,4-cyclohexanedimethanol. One such product contains about 70 weight percent of the trans isomer and about 30 weight percent of the cis isomer. The resultant benzoate ester is commercially available as Benzoflex® 352.

Mixtures of CHDMDB isomers containing from 72 to 99 weight percent of the trans isomer are particularly suitable for use as modifiers in hot melt adhesives based on the processing advantages of faster set time with a sufficiently long open time relative to Benzoflex® 352. Data in the accompanying examples demonstrate that these isomer mixtures also increase the crystallization rate of the resin component of the adhesive by up to two times relative to Benzoflex® 352 in addition to providing stronger bonds. In practical terms, this reduces the time required for development of maximum bond strength.

For applications requiring longer open times than that can be achieved using the trans isomer rich fraction, CHDMDB mixtures containing more than about 34 weight percent of the cis isomer will provide this longer open time.

The types of polymers typically used in hot melt adhesives include but are not limited to ethylene/vinyl acetate copolymers, polyolefins, block copolymers based on styrene, acrylates and olefins, olefins based on metallocene catalysts, amorphous polyalphaolefins, acrylic rubber including acrylic triblocks, ethylene/ethyl acrylate copolymers, polyurethanes of the reactive and non-reactive types, polyesters, sulfopolyesters and polyamides.

The types of tackifying resins used in hot melt adhesives include but are not limited to aliphatic resins, aromatic resins, pure monomer resins, mixed aromatic and aliphatic resins, rosins, rosin esters, terpene and other mixed monomer resins.

When the present CHDMDB isomer mixtures are used in a hot melt adhesive, the concentration range for these mixtures is from 2 to 50 weight percent, preferably from 15 to 35 weight percent, based on the total weight of the adhesive formulation. The optimum concentration is determined by a number of parameters, including but not limited to desired open and set times, melt viscosity, adhesion and strength.

Applications of hot melt adhesives include but are not limited to production of non-woven fabrics, packaging materials, product assembly, book binding adhesives, and adhering of labels. Composite articles may include two bonded layers of materials selected from the group consisting of woven and non-woven fabrics, solid films and sheets formed from natural and synthetic polymers, packaging materials, glue sticks, construction materials, book bindings, and labels. Non-woven fabric may include a diaper or feminine hygiene article. Bonding is achieved using a molten adhesive composition that includes an organic polymer, a resin and a modifier selected from the group consisting of a first mixture containing more than 72 weight percent of the trans isomer of 1,4- cyclohexanedimethanol dibenzoate, preferably 90-94 weight percent of the trans isomer, or a second mixture containing less than 66 weight percent of the trans isomer of 1,4-cyclohexanedimethanol dibenzoate.

The CHDMDB compositions of this invention offer processing and/or product advantages relative to other types of plasticizers and modifiers in a variety of polymer compositions, including but not limited to powder coatings, waterborne coatings, hot melt coatings, solvent-based coatings, u.v. curable coatings, and inks of the jet such as hot melt jet ink, varnish such as overprint varnish, solution and waterborne types.

In this aspect, the benzoate compositions may include organic polymer and a modifier for said polymer. The modifier may include mixtures of the trans and cis isomers of 1,4-cyclohexane-dimethanol dibenzoate, where the trans isomer constitutes from 72 to 99 weight percent of the composition; or mixtures the isomers where the trans isomer constitutes from 1 to 66 weight percent of the composition. The composition may be a plastisol. The composition may be used in engineering plastics for the fabrication of articles by extrusion or injection molding. Further, the composition may include an organic or aqueous vehicle.

The present benzoate compositions act as a processing aid for a variety of plastics, and as both a reinforcing filler and process aid in engineering plastics such as polycarbonates, polyphenylene oxide/styrene blends and similar polymers. As used herein, "processing aides" are materials that can be added in small quantities (1-5%) whereupon substantial improvement results in the processing without significant detraction from other properties. Abstracted from Encyclopedia of PVC Volume II, Page 602 Marcel Dekker, Inc, NY.

The following examples describe the preparation and evaluation of the present isomer mixtures of CHDMDB and should not be interpreted as limiting the scope of the invention as defined in the accompanying claims. Unless otherwise specified all parts and percentages are by weight. Properties of the isomer mixtures and compositions containing these mixtures were measured under ambient conditions.

Example 1

This example describes the preparation of a CHDMDB isomer mixture of the present invention.

100 parts by weight of a CHDMDB isomer mixture containing about 70 weight percent trans-CHDMDB and about 30 percent of the cis isomer, available as Benzoflex® 352 (hereinafter referred to as "control"), were placed in an oven heated to a temperature of 140° C. The temperature of the oven was then lowered to 100° C. and maintained at this temperature for 16 hours. The liquid portion of the composition was decanted, leaving a solid crystalline material. Analysis of the crystalline material by gas chromatography revealed a trans isomer content of 96 percent. This material will be referred to hereinafter as XP-7007

The aforementioned liquid portion solidified at ambient temperature and was found to contain about equal parts by weight of the cis and trans isomers. This material will be referred to hereinafter as XP-7008.

Figure 2:
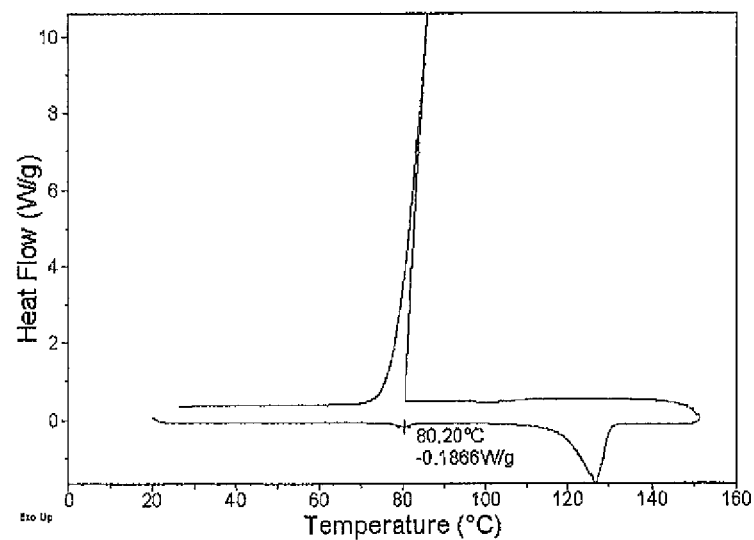
FIG. 2 is a DSC trace of trans rich CHDMDB, XP-7007.
Figure 3:
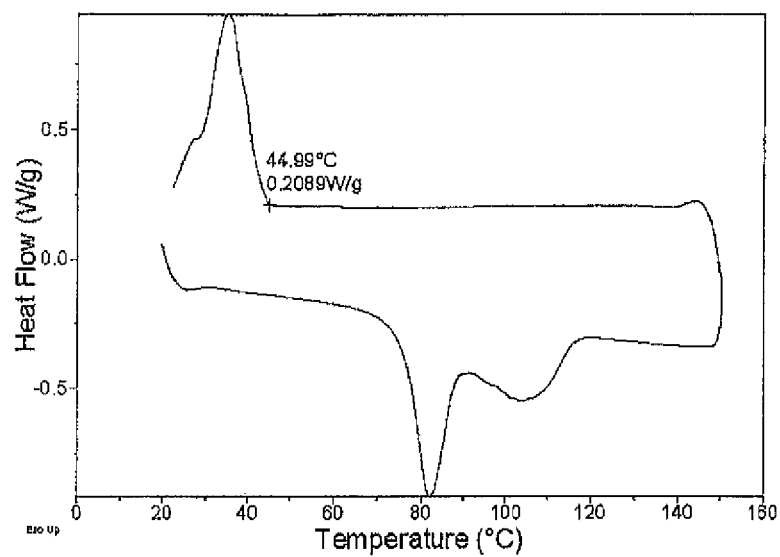
FIG. 3 is a DSC trace of cis rich CHDMDB, XP-7008.

All of the materials were analyzed using a TA model 2910 DSC differential scanning calorimeter. The resultant curves are represented in the accompanying drawings: FIG. 1 for the control, FIG. 2 for XP-7007 and FIG. 3 for XP-7008. The peak for the crystalline XP 7008 material occurs at 80.2° C., considerably higher than the peaks for the commercial ester mixture at 56.77° C. and the considerably broader peak for XP-7008, which is indicative of a higher content of the cis isomer.

Example 2

This example compares the effect on resin crystallization rates of the three CHDMDB isomers of example 1. The five resins evaluated are conventionally used in hot melt adhesives and can be described as follows:

Regelrez® 1094 (Resin A)—A pure monomer aliphatic resin available from Eastman Chemical Wingtack® 95 (Resin B)—A $C_5$ aliphatic resin available from Goodyear Chemical Nevex® 100 (Resin C)—An aromatic resin available from Neville Chemical Eastotac® H-100R (Resin D)—A hydrogenated aliphatic resin available from Eastman Chemical Escorez® 5300 (Resin E)—A cycloaliphatic resin available from Exxon Mobil Chemical Company All samples contained 5 grams of the resin and 5 grams of the isomer mixture.

Crystallization rates were determined using the following procedure: The samples were heated in an oven at 177° C. for 15 minutes, stirred and heated for an additional 15 minutes at the same temperature. The samples were then removed from the oven and allowed to crystallize. The time intervals for initial and complete crystallization are recorded in Table 1.

The isomer mixtures are identified as follows:

1=control=a commercially available mixture identified as Benzoflex® 352 containing a tran:cis isomer weight ratio of 70:30

2=XP 7007 a mixture with a trans:cis weight ratio of 92:8

3=XP 7008 a mixture with a trans trans:cis weight ratio of 1:1

TABLE 1

| Resin | Isomer Mixture | Crystallization Time (minutes) Initial/final |
|---|---|---|
| A | 1 | 2.25/11.5 |
| A | 2 | 1.0/8.5 |
| A | 3 | 4/31 |
| B | 1 | 1.9/15 |
| B | 2 | 1.0/9 |
| B | 3 | 6.2/28 |
| C | 1 | 9/55 |
| C | 2 | 4/35 |
| D | 1 | 3/23 |
| D | 2 | 2/12 |
| E | 1 | 4/25 |
| E | 2 | 2/14 |

The data in Table 1 demonstrate the accelerated rate of crystallization achieved using isomer mixture 2 containing the highest concentration of the trans isomer. The rate of crystallization is retarded relative to the control using the isomer with the highest cis isomer content, which may be desirable for some commercial applications.

Example 3

This example compares the properties imparted to various formulations by the benzoate isomer mixture of this invention with those imparted by a known isomer mixture.
Preparation of Adhesive Formulations All of the adhesive formulations were prepared by melting the ingredients other than the polymer at 177° C. while mixing at low speed (400 RPM's). The polymer was then added in slowly and mixed until homogeneous, which required a maximum mixing time of 30 minutes. If degassing was required, the adhesive formulation was placed in a can and heated for one hour in an oven.

Composition of Adhesive Formulations

Formulation 1. A Block Copolymer Construction Adhesive for Non-woven Fabrics 50 parts of Regelrez® 1094—A pure monomer aliphatic resin available from Eastman Chemical 0.5 parts of Inorgox®1010—an antioxidant available from Ciba Geigy Corporation 35 parts of the isomeric CHDMDB to be evaluated, identified as described in Example 1.

25 parts of Kraton® G-1652, a styrene/ethylene/butadiene/styrene copolymer available from Kraton Polymers Formulation 2. A Palletizing Adhesive 10 parts of an ethylene/vinyl acetate copolymer available as Elvax® 150 from Dupont 50 parts of an aromatic resin available from Neville Chemical as Nexex® 100

50 parts of the CHDMBD isomer mixture to be evaluated 1 part of Irganox® 1076,

Formulation 3. A Typical Glue Stick Formulation 25 parts of a 400 melt index ethylene/vinyl acetate copolymer containing 28 mole percent of vinyl acetate, available as Elvax® 210 from Dupont 21 parts of 4 melt index ethylene/vinyl acetate copolymer containing 28 mole percent of vinyl acetate, available as Elvax® 260 from Dupont 35 parts of Sylvatac® 100 NS, a rosin ester available from Arizona Chemical 20 parts of the CHDMDB isomer mixture to be evaluated 0.1 part of an antioxidant available as Irganox® 101 from Ciba Geigy Corporation Formulation 4. A Typical Label and Generic Packing Glue 25 parts Elvax® 210

25 parts of Sylvatac® 100 NS 25 parts of the CHDMDB isomer 0.1 part of an antioxidant available as Irganox® 1010 from Ciba Geigy 3 parts of mineral oil available as Tufflo 6056 from Citco Formulation 5. An Adhesive for Nonwoven Applications Based on Metallocene Polyolefins 37 parts of metallocene catalyzed polyolefin available as Licocene®PP2602 from Clariant 3 parts of metallocene catalyzed polyolefin available as Licocene® PE4201

20 parts of the CHDMDB isomer 40 parts of cycloaliphatic resin available as Escorez® 5300 from, Exxon Mobil 0.1 part of Irganox® 1010

Test Procedures

Average open times, based on a minimum of 3 measurements, were determined using 2 inch-wide strips of Kraft paper. The formulation to be evaluated was heated to 177° C. in an oven. A 10 mil-thick film of the molten adhesive was applied to the paper strip using a 3 inch-long Bird draw-down bar and a timer was started. A second strip of Kraft paper was applied over the adhesive at the desired time interval using a back and forth stroke with a 50 gram wood block and immediately removed. This procedure was repeated at longer time intervals until no fiber-tearing bonds were observed. The time interval at which this occurred was recorded and appears in Table 2.

Average set times, based on a minimum of three measurements, were determined by applying the molten formulation being evaluated to a 3½ inch wide strip of Kraft paper using a 3 inch-wide Bird draw down bar. The formulation had been heated to a temperature of 177° C. in an oven. A 10-mil thick film of the adhesive was applied to the paper strip using a draw down bar and a second paper strip was applied followed by hand pressure. The upper layer of paper was pulled away at a constant rate. The time interval at which tearing of the paper fiber was first observed was noted and recorded as the set time. The set time values appear in Table 3.

Adhesion to a variety of substrates was determined by applying the molten formulation to a sheet of 110-pound lithographic paper and allowing the coating to solidify. The coated paper was cut into 2 by 2 inch (5 cm. by 5 cm.) squares and the coated side applied to glass, white pigmented (W) or clear (C) PVC (polyvinyl chloride), steel, aluminum and oak. The coated paper was heated with a hot air blower to activate the adhesive, following which the resultant composite was allowed to cool. The cooled paper was pulled off the substrate and the percentage of torn paper fibers was evaluated.

The temperature at which adhesion failed due to shearing forces (SAFT; shear adhesion fail temperature) was determined by applying a 6 mil thick layer of the molten adhesive to be evaluated on to a piece of Mylar® film. When the adhesive cooled a 1-inch by 6-inch strip of the film was applied to a sheet of stainless steel to form a 1-inch by 1-inch lap joint. The area of overlap was then heated with a hot air gun to melt the adhesive, forming the bond. The free end of the film strip was attached to a one kilogram weight using a paper clip. The resultant composite was then attached to a support with sufficient clearance to allow the weight to fall. The assembly was then placed in an oven heated to 50° C. The oven temperature was increased by 5° C. every half hour. The temperature at which the weight fell was noted.

The temperature of adhesion failure was determined for adhesive formulation 2 (the palletizing adhesive) by application of a 3/16 inch-diameter bead of this formulation to a 2" by 16"piece of corrugated cardboard. The adhesive was used to form a bonded laminate with a 2"×2" piece of laminated cardboard. At one-minute intervals the strength of the bond was determined. The time required for complete bond failure was recorded.

Melt viscosity values were obtained at 177° C. using a model DV II RVT Brookfield viscometer equipped with a Thermosel® apparatus and a number 18 spindle rotating at a speed of 5 RPM was selected to determine apparent viscosity.

The results of the evaluations are recorded in the following tables. The samples of CHDMDB are identified as "Control" for the commercial material, XP-007 for the mixture containing 96 percent of the trans isomer and XP 008 for the material containing substantially equal weights of the trans and cis isomers.

Melt Viscosity (mPa·s) at 177° C.

TABLE 2

| Formulation | Control | XP 7007 | XP 7008 |
| --- | --- | --- | --- |
| 1 | 4819 | 3084 | 3402 |
| 2 | 467 | 204 | 198 |
| 3 | 9177 | 9382 | 12680 |
| 4 | 358 | 140 | 435 |
| 5 | 1011 | 1100 | 7008 |

TABLE 3

Average Open Time

| Formulation | Control | XP 7007 | XP 7008 |
|---|---|---|---|
| 1 | 107 s | 23 s | 222 sec |
| 2 | 3.8 m | 1.2 m | 9.6 min |
| 3 | 4.5 m | 2 m | 12.6 m |
| 4 | <10 s | <5 sec | <10 s |
| 5 | 60 s | 60 s | 96 s | s = seconds
m = minutes

TABLE 4

Average Set Time (Seconds)

| Formulation | Control | XP 7007 | XP 7008 |
|---|---|---|---|
| 1 | 4 | 2 | 5 |
| 3 | 16 | 15 | 21 |
| 4 | 3 | <3 | 4 |
| 5 | 23 | 25 | 23 |

TABLE 5

Adhesion

| Formulation | Substrate | Control | XP 7007 | XP 7008 |
|---|---|---|---|---|
| 1 | A | 100% fiber tear | 100% fiber tear | 100% fiber tear |
| 3 | B | 100% fiber tear | 100% fiber tear | 100% fiber tear |
|  | C | 100% fiber tear | 50% fiber tear | 100% fiber tear |
|  | D | 100% fiber tear | 100% fiber tear | 100% fiber tear |
|  | F | 100% fiber tear | 100% fiber tear | 100% fiber tear |
|  | G | 100% fiber tear | 100% fiber tear | 100% fiber tear |
|  | H | 100% fiber tear | 90% fiber tear | 60% fiber tear |
| 4 | B | Heavy fiber displacement, no transfer | Small degree of fiber displacement; No tearing | 50% fiber tearing |

Substrates:
A = diaper stock;
B = glass;
C = white PVC;
D = clear PVC;
E = steel;
F = aluminum;
G = oak

TABLE 6

Temperature of Adhesion Failure Due To Shearing Forces (SAFT) (° C.)

| Formulation | Control | XP 7007 | XP 7008 |
|---|---|---|---|
| 1 | 60° | 75° | 60° |
| 3 | 60° | 60° | 55° |

TABLE 7

Time Interval To Adhesion Failure of Palletizing Adhesive

| Formulation 2 | Control | XP 7007 | XP 7008 |
|---|---|---|---|
| 2 | 4 minutes | <1 minute | 8 minutes |

We claim:

1. A method for accelerating a set time and crystallization rate of a hot melt adhesive composition comprising selecting a modifier comprising 1,4-cyclohexanedimethanol dibenzoate containing 90 to 94 weight percent trans isomer and formulating said hot melt adhesive composition comprising said modifier, a tackifying resin, and a thermoplastic polymer, wherein said tackifying resin is selected from the group consisting of rosin esters, aliphatic resins, and aromatic resins and said thermoplastic polymer is selected from the group consisting of ethylene/vinyl acetate copolymers, polyolefins, and styrenic block copolymers.

2. The method of claim 1 wherein said formulating comprises heating said modifier and said tackifying resin together to form a melt and adding said thermoplastic polymer to said melt.

3. The method of claim 1 wherein said tackifying resin consists of said rosin esters.

4. The method of claim 1 wherein said thermoplastic polymer consists of said ethylene/vinyl acetate copolymers.

* * * * *